United States Patent [19]

Lane et al.

[11] Patent Number: 4,725,274
[45] Date of Patent: Feb. 16, 1988

[54] PROSTHETIC HEART VALVE

[75] Inventors: Ernest Lane, Huntington Beach; Hung L. Lam, Fullerton, both of Calif.

[73] Assignee: Baxter Travenol Laboratories, Inc., Deerfield, Ill.

[21] Appl. No.: 923,083

[22] Filed: Oct. 24, 1986

[51] Int. Cl.⁴ .............................................. A61F 2/24
[52] U.S. Cl. ....................................................... 623/2
[58] Field of Search .................................... 623/2, 900

[56] References Cited

U.S. PATENT DOCUMENTS

| | | |
|---|---|---|
| 4,084,268 | 4/1978 | Ionescu et al. |
| 4,106,129 | 8/1978 | Carpentier et al. ............ 623/2 |
| 4,172,295 | 10/1979 | Batten . |
| 4,345,340 | 8/1982 | Rosen . |
| 4,364,126 | 12/1982 | Rosen et al. |
| 4,388,735 | 6/1983 | Ionescu et al. |
| 4,441,216 | 4/1984 | Ionescu et al. |
| 4,470,157 | 9/1984 | Love . |
| 4,491,986 | 1/1985 | Gabbay . |
| 4,506,394 | 3/1985 | Bedard . |

FOREIGN PATENT DOCUMENTS 0150608 12/1984 European Pat. Off. .

Primary Examiner—Richard J. Apley
Assistant Examiner—James Prizant
Attorney, Agent, or Firm—Gordon L. Peterson

[57] ABSTRACT

A prosthetic heart valve comprising a frame which includes outer and inner bands and a plurality of wirelike members interlocked with the bands and forming the tip portions of commissure supports. The bands are covered with outer and inner jackets, and valve leaflets are attached to the frame and extend over a distal edge of the bands. The ends of the jackets form flexible, resilient fingers which extend between the distal edge and the valve leaflets to shield the valve leaflets from the distal edge.

19 Claims, 15 Drawing Figures

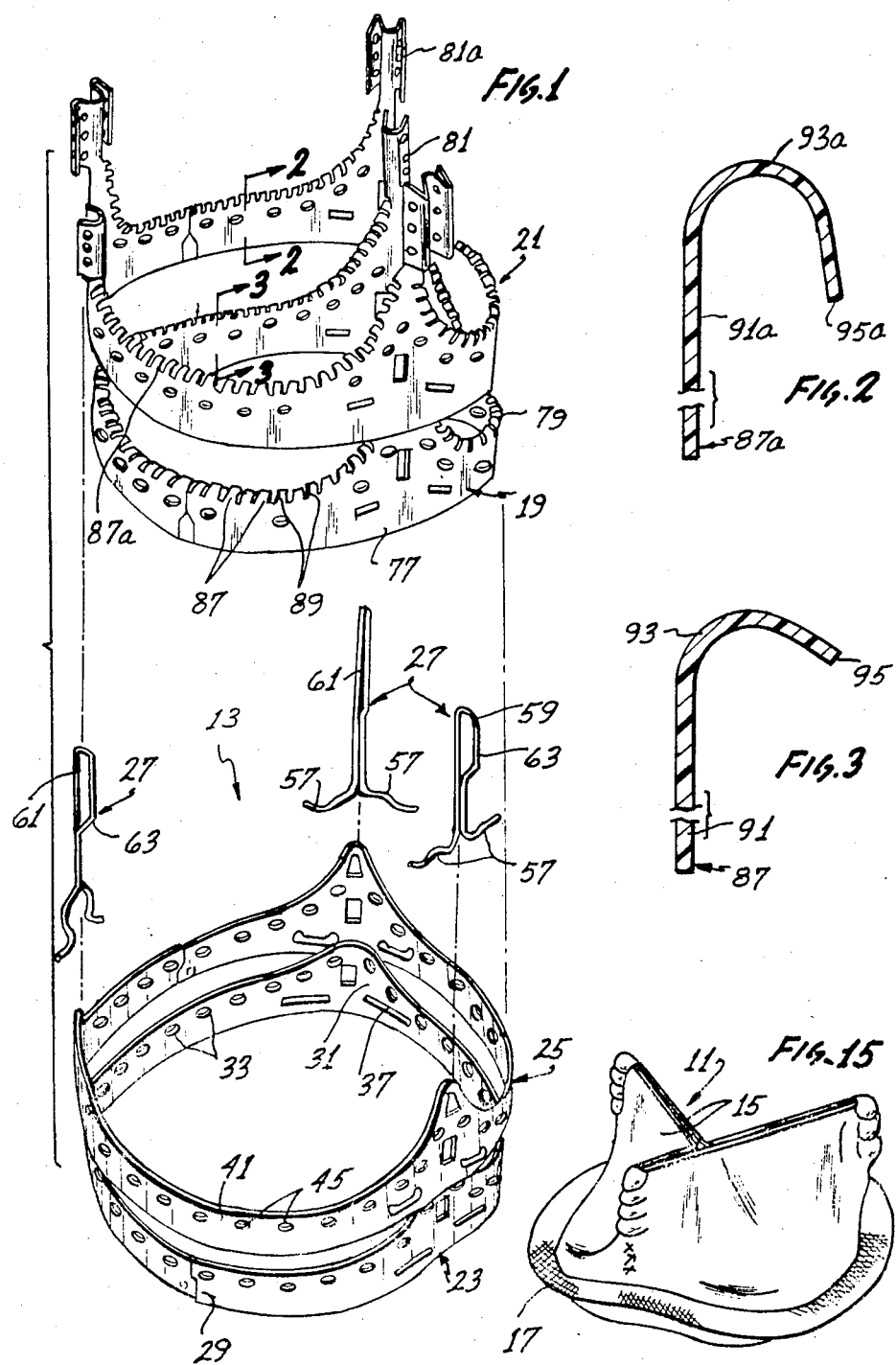

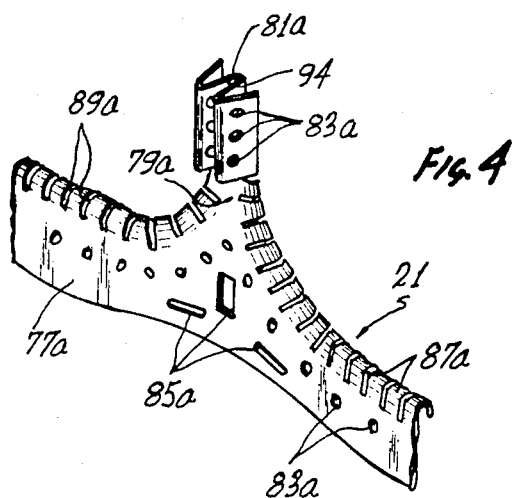
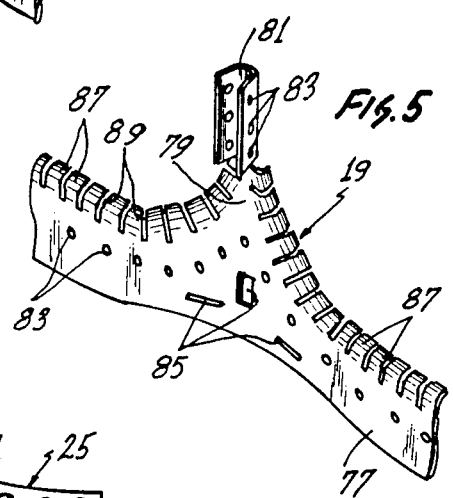
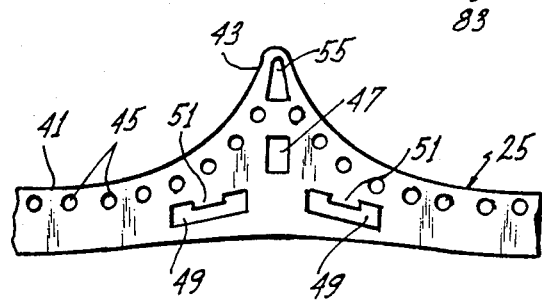
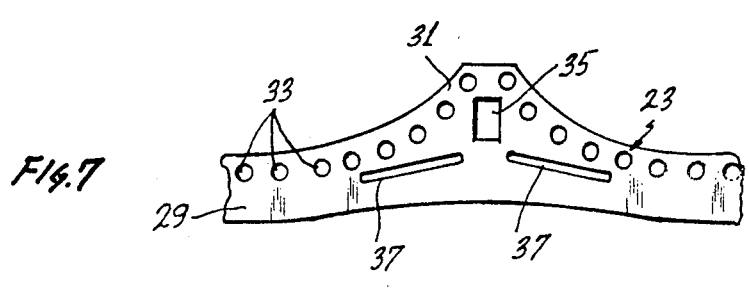

PROSTHETIC HEART VALVE

BACKGROUND OF THE INVENTION

Prosthetic heart valves are now widely used to replace natural diseased valves of the human heart. Prosthetic heart valves are either of the mechanical or leaflet type.

A leaflet-type prosthetic heart valve typically includes a frame or stent, valve leaflets coupled to the frame and a sewing ring to enable the valve to be sutured into the heart at an appropriate location. The frames are typically constructed of wire as shown, for example, in Carpentier et al U.S. Pat. No. 4,106,129 or of sheet material as shown, for example, by Ionescu et al U.S. Pat. No. 4,084,268. In either event, the properties of the base and commissure supports are derived from the same construction, i.e., a wire or sheet material. Unfortunately, it is sometimes desirable that the commissure supports and the base have different properties or characteristics. Thus, the selection of the particular wire or sheet material of necessity represents a compromise between the desired properties of the commissure supports and the base.

For example, an all-wire frame may have a base which is too deformable. Conversely, a sheet material frame may provide commissure supports which are too rigid and tend to cause tearing of the valve leaflets.

In addition, to make a wire frame, opposite ends of an elongated wire must be joined together to form an annular frame. The splicing together of the opposite ends of the wire forms a discontinuity in the frame which can be troublesome.

In a leaflet-type prosthetic heart valve, it is necessary that the valve leaflets extend over an outflow edge or distal edge of the frame. When implanted, the valve leaflets repeatedly open and close, and this causes some abrasion of the valve leaflets by the distal edge. It is known to pad the distal edge of the frame as shown, for example, in Ionescu et al U.S. Pat. No. 4,084,268 and in European Patent Application No. 0150608. However, prior art padding techniques have not been as sufficient as desired in reducing abrasion of the valve leaflets because the pad is believed to lose its cushioning ability after long periods of use.

SUMMARY OF THE INVENTION

This invention solves these problems. To provide a frame having different properties at the base and at least the tip portions of the commissure supports, this invention provides a frame which includes band means for forming a band-like base for the frame and a plurality of commissure supports joined to the base and extending axially thereof with at least one of the commissure supports including an elongated member.

This construction enables the base to be semi-rigid, and the commissure supports to be more flexible. The semi-rigid nature of the base is desirable to avoid deformation of the base in some situations, and the resilience of the commissure supports is desirable during valve operation to reduce the likelihood of tearing the valve leaflets.

If the elongated member were welded to the band means, there is a possibility that the weld would change the characteristics of the material, and the joint may break. Accordingly, to avoid having to weld, the band means has opening means defining at least one opening and a region of the elongated member is received in the opening means and is interlocked therewith to attach the elongated member to the band means. This enables the elongated member to be joined to the band means without welding and to extend generally axially beyond the band means and form at least a tip portion of a commissure support.

The prosthetic heart valve also includes valve leaflets attached to the frame and extending over a distal edge of the base. To reduce leaflet abrasion and to cushion the leaflet closing shock more effectively, this invention provides a plurality of resilient, flexible fingers which extend between the distal edge and the valve leaflets for shielding the valve leaflets from the distal edge. These flexible fingers are not expected to lose their resilience or their ability to cushion even after prolonged periods of use.

The elongated member, which is attached to the band means, can advantageously include an elongated wire-like member having opposite end portions and a reverse bend. The opposite end portions are received in the opening means of the band means and interlock therewith. A reverse bend forms a distal end of the tip portion of the associated commissure support. Preferably, each of the commissure supports is formed in this fashion.

The band means preferably includes outer and inner bands. The two bands add rigidity to the base and provide for a greater degree of security in the interlocking attachment to the elongated member. In addition, the outer band preferably extends axially beyond the inner band at the commissure supports to form a portion of each of the commissure supports. With this construction, each commissure support includes at least a region of the outer band and the elongated member, with the outer band projecting beyond the inner band, and the elongated member projecting beyond the outer band. This provides, in effect, a multiple leaf spring having desirable flexure characteristics.

Although a single set of the resilient, flexible fingers provide desirable protection against abrasion and cushioning of shock loading, for even better results, the fingers are arranged in outer and inner sets. When this is done, the fingers of the inner set can support the fingers of the outer set for at least a portion of the lengths of the fingers of the outer set. Preferably, the fingers of the inner set extend between the distal edge and the fingers of the outer set. This forms, in effect, a multiple leaf spring in which the leaves of the spring, i.e., the fingers of the two sets, are slidable relative to each other. The multiple leaves provide the advantage of giving a more linear deflection in response to load than could ordinarily be obtained from a single leaf. The outer end portions of the fingers are preferably curved to provide a smooth curved edge over which the valve leaflets can extend. When the valve leaflets close, the fingers are resiliently deflected by the valve leaflet closing force, and they preclude the valve leaflet from being abraded by the distal edge of the frame and cushion the closing action of the leaflets.

The fingers can advantageously be provided as portions of one or more jackets which cover at least a major portion of the frame. In a preferred construction, outer and inner jackets are provided, with the outer jacket providing the outer set of fingers and the inner jacket providing the inner set of fingers.

The invention, together with additional features and advantages thereof, can best be understood by reference to the following description taken in connection with the accompanying illustrative drawing.

BRIEF DESCRIPTION OF THE DRAWING

FIG. 1 is an exploded isometric view of a frame and jackets constructed in accordance with the teachings of this invention.

FIGS. 2 and 3 are sectional views taken along lines 2—2 and 3—3, respectively, of FIG. 1.

FIGS. 4 and 5 are side isometric views of portions of the outer and inner jackets, respectively, adjacent one of the commissures and laid out flat.

FIGS. 6 and 7 are fragmentary side elevational views of portions of the outer and inner bands adjacent to one of the commissures and laid out flat.

FIG. 15 is an isometric view of a prosthetic heart valve constructed in accordance with the teachings of this invention.

DESCRIPTION OF THE PREFERRED EMBODIMENT

Figure 8:
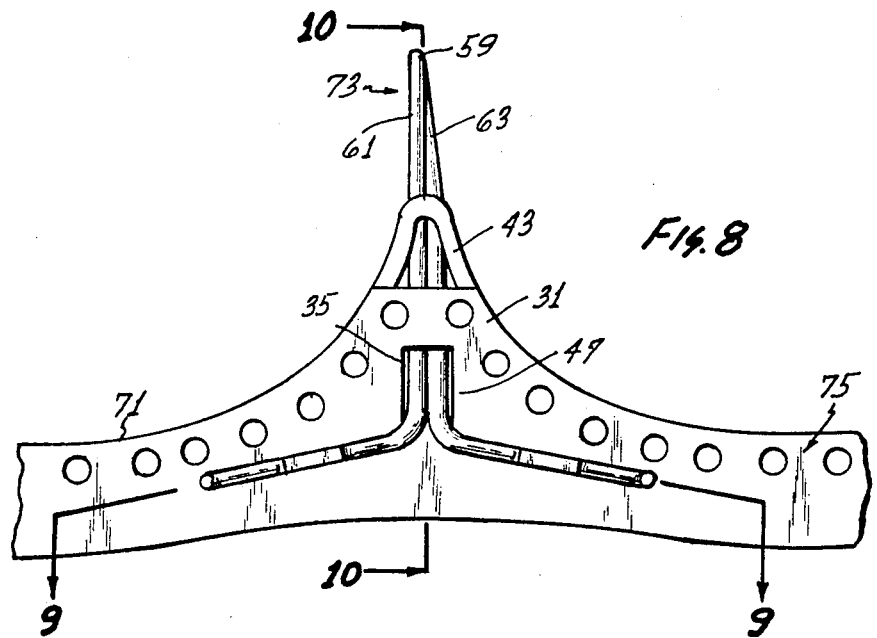
FIG. 8 is a fragmentary side elevational view of a region of the inside of the assembled frame adjacent one of the commissures with the frame laid out flat. The jackets are not shown in FIG. 8.

FIG. 15 shows a prosthetic heart valve 11 which generally comprises a frame or stent 13 (FIG. 1), valve leaflets 15 attached to the frame, a suture ring 17 attached to the frame and inner and outer jackets 19 and 21 (FIG. 1) covering the frame. The frame 13 generally comprises band means in the form of an inner band 23 and an outer band 25 (FIGS. 1, 6 and 7) and elongated members in the form of elongated wire members 27.

Each of the bands 21 and 23 can be constructed of a suitable biocompatible metal or plastic, with a metal known as Elgiloy being preferred. Both of the bands 23 and 25 are formed from a flat strip of sheet material which is formed into an annular configuration and welded together at its opposite ends.

The inner band 23 has a base section 29 and three commissure portions 31 which are equally spaced circumferentially and which project generally axially of the base section 29 (FIGS. 1 and 7). The inner band 23 has a series of suture holes 33 extending completely around the band and interlocking openings in the form of an upper interlocking opening 35 and a pair of lower interlocking openings or slots 37. One set of the openings 35 and 37 is provided at each of the commissure portions 31, and thus the illustration in FIG. 7 is typical.

The outer band 25 is similar to the inner band 23, and it includes a base section 41 and three commissure portions 43 which are equally spaced circumferentially and which extend generally axially of the base section 41. The outer band 25 has a series of suture holes 45 which extend completely around the band and, at each of the commissure portions 43 has opening means in the form of an upper interlocking opening 47 and a pair of lower openings or slots 49 (FIG. 6). Tabs 51 project downwardly into each of the slots 49, and an opening 55 is provided at each of the commissure portions 43.

Each of the wire-like members 27 is identical and may be constructed of a wire of a suitable biocompatible material with metal being preferred. Elgiloy is the preferred metal because of its stiffness, grain orientation and strength.

Figure 10:
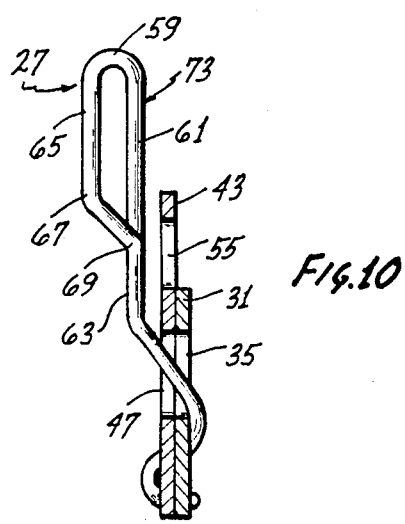

Each of the wire-like members 27 includes opposite end portions 57 and a reverse bend 59 midway between the end portions. The end portions 57 are joined to the reverse bend 59 by axial segments 61 and 63 (FIGS. 1, 8 and 10), and the end portions 57 form nearly a 90-degree angle with the associated segments 61 and 63. Near the reverse bend 59, the segments 61 and 63 are shaped to form a loop 65 as best shown in FIG. 10, and in this embodiment, this is accomplished in part by a pair of bends 67 and 69 in the segment 63.

Figure 14:
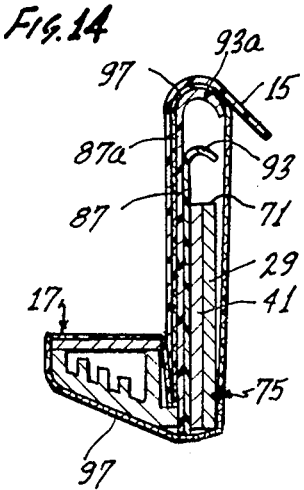

In the assembled condition of the frame 13, the base sections 29 and 41 are coextensive as shown in FIG. 14 and form a base 75 (FIG. 8) for the frame, with the base having a distal edge 71. The suture holes 33 and 45 are in registry, respectively, and lie adjacent the distal edge 71. The openings 35 and 37 of each commissure portion 31 are in substantial registry with the openings 47 and 49, respectively, of an associated commissure portion 43. The commissure portions 31 and 43 are in radial alignment; however, the commissure portion 43 projects axially or distally of the commissure portion 31 as shown in FIGS. 8 and 10.

Figure 9:
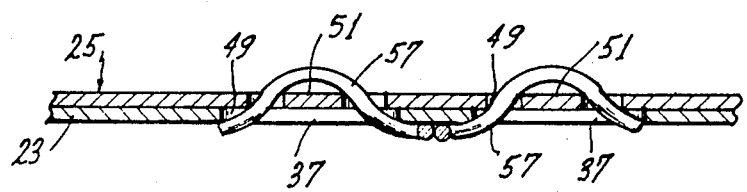
FIGS. 9 and 10 are fragmentary sectional views taken generally along line 9—9 and 10—10, respectively, of FIG. 8.

Each of the wire members 27 is attached to the bands 23 and 25 at the commissure portions 31 and 43 and extends generally axially beyond the commissure portions 43 to form a tip portion of a commissure support 73 (FIG. 10) of the frame 13. The attachment of the wire member 27 to the bands 23 and 25 is by interlocking the wire member to the bands as shown in FIGS. 8-10. More specifically, the segments 61 and 63 project through the openings 35 and 47 (FIG. 10). The end portions 57 are shaped as necessary to extend through the slots 37, the slot 49, around the tab 51, back out through the slot 49 and back through the slot 37 as shown in FIG. 9. This securely attaches each of the wire members 27 to the bands 23 and 25.

For assembly purposes, the bands 23 and 25 may be first joined together as by suitable welds. The wire members 27 can then be assembled into the appropriate openings of these bands as described above.

When constructed in this fashion, the bands 23 and 25 make the base 75 semi-rigid. The commissure supports 73 are, however, relatively resilient and can be flexed radially of the base 75. In this regard, each of the wire members 27 and the associated commissure portions 31 and 43 serve, in effect, as a leaf spring with multiple leaves to oppose the radial inward movement of the associated valve leaflets 15.

The jackets 19 and 21 are essentially identical and substantially completely cover the outer surface of the frame 13. The jackets 19 and 21 are preferably constructed of a biocompatible plastic material, such as Mylar.

Figure 13:
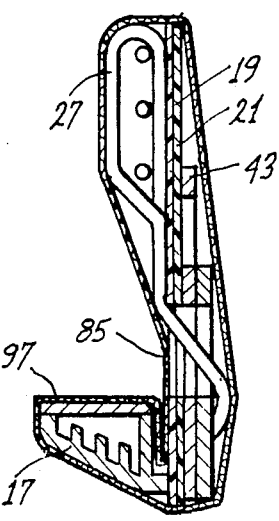
FIGS. 13 and 14 are sectional views taken generally along line 13—13 and line 14—14, respectively, of FIG. 12.

The inner jacket 19 has a base section 77 (FIGS. 1 and 5) and three equally spaced commissure sections 79 projecting from the base section. The jackets 19 and 21 may be made by cutting and/or punching a flat plastic strip to the desired configuration. End portions of the strip can then be appropriately joined together to form the jackets 19 and 21 into an annular configuration. Each of the commissure sections 79 terminates distally in a wide tab 81 of generally U-shaped configuration. The jacket 19 has suture holes 83 and openings 85 to accommodate the wire members 27 as shown in FIG. 13. The jacket 19 also includes a plurality of resilient, flexible fingers 87 projecting outwardly along the distal edge of the base section 77 and a portion of the commissure sections 79. The fingers 87 are separated by narrow slots 89.

As shown in FIG. 3, each of the fingers 87 includes a linear first section 91, a curved outer section 93 and a distal end 95. Although this configuration is preferred, it should be taken as merely illustrative of many different configurations that may be employed for the fingers 87.

The outer jacket 21 (FIGS. 1 and 4) is substantially identical to the inner jacket 19, and portions of the jacket 21 corresponding to portions of the jacket 19 are designated by corresponding reference numerals followed by the letter "a." The tab 81a of the jacket 21 is generally W-shaped in cross section and has suture holes 83a and a central section 94 as shown in FIG. 4. The primary difference, however, is that the fingers 87a have a linear section 91a (FIG. 3) that is longer than the linear section 91 of the fingers 87. In addition, the curved outer section 93a curves through a larger angle than the curve 93 as shown in FIG. 3. The curved outer section 93 eliminates any sharp edge that might tend to abrade or cut the confronting fingers 87a.

Figure 11:
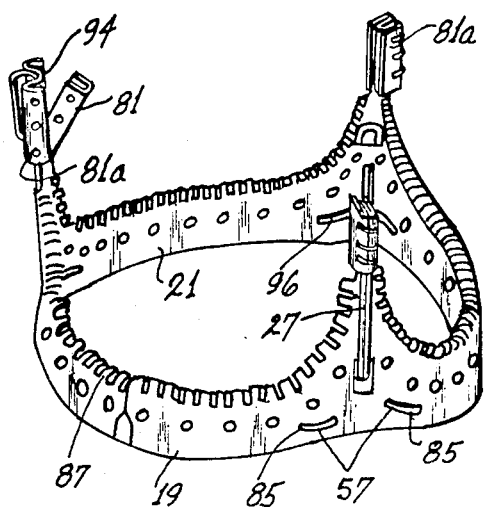
FIG. 11 is an isometric view of the frame-jacket assembly in nearly completed form, except at one of the commissure tip portions.

With the frame 13 assembled as described above so that the wire members 27 are interlocked with the bands 23 and 25, the jackets 19 and 21 can then be placed over the frame. For example, the inner jacket 19 can be slid down over the frame 13 by inserting the reverse bends 59 of the wire members 27 through the central opening 85a of each of the commissure sections 79a. The jacket 19 is slid downwardly until it is essentially coextensive with the bands 23 and 25. Next, the outer jacket 21 is similarly slid down over the inner jacket 19 by placing the reverse bends 59 of the wire members 27 through the central or uppermost opening 85 of each of the commissure sections 79. This places the jackets 19 and 21 between the wire-like members 27 and the commissure portions 43 as shown in FIG. 13. The tabs 81 and 81a receive the distal regions of the wire members 27 as shown in FIG. 11 and are held in position by sutures 96 to thereby affix the jackets 19 and 21 to the frame 13. Specifically, the central region of the tab 81a receives the distal region of the associated wire member 27, and the central region is received by the U-shaped tab 81. In addition, the end portions 57 of the wire members 27 project through the outer aligned openings 85 and 85a of confronting commissure sections 79 and 79a to further tend to interlock the jackets 19 and 21 to the frame 13.

Each of the fingers 87a extends above an associated finger 87 as shown in FIG. 14. Thus, the fingers 87a form an outer set of fingers. The fingers 87 form an inner set of fingers. The fingers 87 of the inner set extend between the distal edge 71 and the fingers 87a of the outer set. Also, the fingers 87 of the inner set extend along and support the fingers 87a of the outer set for a portion of the lengths of the fingers of the outer set as shown in FIG. 14. The curved sections 93 and 93a open toward the distal edge 71.

Figure 12:
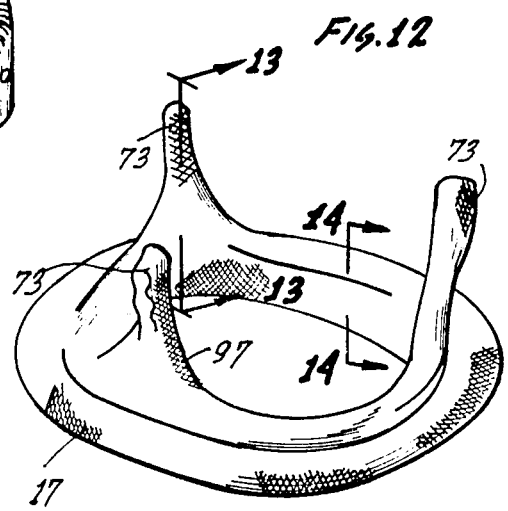
FIG. 12 is an isometric view of the completed frame-jacket assembly covered with cloth and attached to a suture ring.

The suture ring 17, which may be of conventional construction, is attached to the base 75 in a conventional manner. A layer of cloth 97 (FIGS. 13 and 14) covers the entire frame, jackets 19 and 21 and the suture ring as shown in FIG. 12 to form a stent to which the valve leaflets 15 are attached with sutures in a conventional manner. The sutures may extend through the suture holes 33, 45, 83 and 83a. These suture holes form a single row of holes for this purpose. As shown in FIG. 14, the fingers 87 and 87a extend between the distal edge 71 and the valve leaflets 15 for shielding the valve leaflets from the distal edge. The fingers 87 and 87a form a leaf spring containing multiple leaves which provide for a more linear deflection in response to radial inward loads. The fingers 87 and 87a resiliently deflect in response to radial inward loads to cushion the movement of the valve leaflets toward the distal edge 71, as well as to shield the leaflets from the metal forming the distal edge. The jackets 19 and 21 separate the cloth 97 from the exterior of the bands 23 and 25, and the cloth 97 provides smooth, soft, continuous layer between the leaflets 15 and the fingers 87a. The curved outer sections 93a of the fingers 87a provide a broad, smooth, curved surface for supporting the valve leaflets to thereby reduce stress on the valve leaflets along the distal edge 71.

Although an exemplary embodiment of the invention has been shown and described, many changes, modifications and substitutions may be made by one having ordinary skill in the art without necessarily departing from the spirit and scope of this invention.

We claim:

1. A prosthetic heart valve comprising:
a frame including band means for forming a generally annular band-like base for the frame and a plurality of commissure supports joined to said base and extending generally axially thereof;
at least one of said commissure supports including an elongated member;
said band means having opening means defining at least one opening in the band means;
a region of said elongated member being received in said opening means and cooperating therewith to attach said elongated member to said band means so that the elongated member can extend generally axially beyond the band means and form at least a tip portion of said one commissure support; and
valve leaflets attached to said frame.

2. A valve as defined in claim 1 wherein said elongated member includes an elongated wire-like member having opposite end portions and a reverse bend, said opposite end portions are received in said opening means and cooperate therewith to attach said elongated member to said band means and said reverse bend forms a distal end of said tip portion of said one commissure support.

3. A valve as defined in claim 1 wherein said band means includes outer and inner bands.

4. A valve as defined in claim 3 wherein said opening means forms openings in both of said outer and inner bands and said region of the elongated member is received in the openings of the outer and inner bands.

5. A valve as defined in claim 3 wherein the outer band extends generally axially beyond the inner band at said one commissure support to form a portion of said one commissure support.

6. A valve as defined in claim 5 wherein said elongated member includes an elongated wire-like member having opposite end portions and a reverse bend, said opposite end portions are received in said opening means and cooperate therewith to attach said elongated member to said band means and said reverse bend forms a distal end of said tip portion of said one commissure support.

7. A valve as defined in claim 1 wherein said band means has a distal edge and the heart valve includes means defining a plurality of resilient, flexible fingers extending between said distal edge and said valve leaflets.

8. A valve as defined in claim 7 wherein said fingers are arranged in outer and inner sets and the fingers of the inner set support the fingers of the outer set for a portion of the lengths of the fingers of the outer set.

9. A valve as defined in claim 8 including outer and inner jackets of sheet material, said jackets covering a major portion of said frame, and said defining means including regions of said jackets.

10. A value as defined in cliam 9 wherein said elongated member includes an elongated wire-like member having opposite end portions and a reverse bend, said opposite end portions are received in said opening means and cooperate therewith to attach said elongated member to said band means, said reverse bend forms a distal end of said tip portion of said one commissure support, and said band means includes outer and inner bands.

11. A prosthetic heart valve comprising:
a frame including a generally annular base and a plurality of commissure supports joined to said base and extending generally axially thereof, said base having a distal edge;
valve leaflets attached to said frame and extending over said distal edge; and
means defining a plurality of resilient, flexible fingers which extend between said distal edge and the valve leaflets for shielding the valve leaflets from said distal edge, at least some of said flexible fingers being between the commissure supports.

12. A valve as defined in claim 11 wherein said fingers are arranged in outer and inner sets and the fingers of the inner set extend between said distal edge and the fingers of the outer set.

13. A valve as defined in claim 11 wherein said fingers are arranged in outer and inner sets and the fingers of the inner set support the fingers of the outer set for a portion of the length of the fingers of the outer set.

14. A valve as defined in claim 11 including a jacket of sheet material covering at least a major portion of the frame, said jacket including said defining means.

15. A valve as defined in claim 14 wherein said frame includes band means defining said base and said jacket covers a major portion of the band means.

16. A valve as defined in claim 11 including outer and inner jackets of sheet material, said jackets covering a major portion of said frame, and said defining means including regions of said jackets.

17. A valve as defined in claim 11 including a cloth layer between the fingers and the valve leaflets.

18. A prosthetic heart valve comprising:
a frame including a generally annular base and a plurality of commissure supports joined to said base and extending generally axially thereof, said base having a distal edge;
valve leaflets attached to said frame and extending over said distal edge;
means defining a plurality of resilient, flexible fingers which extend between said distal edge and the valve leaflets for shielding the valve leaflets from said distal edge; and
said fingers being arranged in outer and inner sets and the fingers of the inner set extending between said distal edge and the fingers of the outer set.

19. A prosthetic heart valve comprising:
a frame including a generally annular base and a plurality of commissure supports joined to said base and extending generally axially thereof, said base having a distal edge;
valve leaflets attached to said frame and extending over said distal edge;
means defining a plurality of resilient, flexible fingers which extend between said distal edge and the valve leaflets for shielding the valve leaflets from said distal edge; and
said fingers being arranged in outer and inner sets and the fingers of the inner set support the fingers of the outer set for a portion of the length of the fingers of the outer set.

* * * * *